US007135454B2

(12) United States Patent
Chimienti et al.

(10) Patent No.: US 7,135,454 B2
(45) Date of Patent: Nov. 14, 2006

(54) USE OF SLURP-1 COMPOSITIONS FOR TREATING SCHIZOPHRENIA

(75) Inventors: Fabrice Chimienti, Lausanne (CH); Ronald Hogg, Genève (CH); Marcel Huber, Lausanne (CH); Daniel Bertrand, Genève (CH); Daniel Hohl, Lusanne (CH)

(73) Assignee: Applied Research Systems ARS Holding N.V. (NL)

( * ) Notice: Subject to any disclaimer, the term of this patent is extended or adjusted under 35 U.S.C. 154(b) by 0 days.

(21) Appl. No.: 10/826,788

(22) Filed: Apr. 16, 2004

(65) Prior Publication Data

US 2005/0004025 A1    Jan. 6, 2005

Related U.S. Application Data

(60) Provisional application No. 60/463,418, filed on Apr. 16, 2003.

(51) Int. Cl.
*A61K 38/19*   (2006.01)
*C07K 14/52*   (2006.01)

(52) U.S. Cl. .............................. 514/2; 514/12; 530/350

(58) Field of Classification Search ..................... None
See application file for complete search history.

(56) References Cited

U.S. PATENT DOCUMENTS

| 5,298,604 A | 3/1994 | Sloane ........................ 530/351 |
| 5,908,827 A | 6/1999 | Sirna ............................ 514/12 |

FOREIGN PATENT DOCUMENTS

| EP | 0 675 956 B1 | 10/1995 |
| EP | 0 895 478 B1 | 2/1999 |
| EP | 1 093 380 B1 | 4/2001 |
| WO | WO 98/56810 | 12/1998 |

OTHER PUBLICATIONS

Arredondo et al. (2002). Central role of alpha7 nicotinic receptor in differentiation of the stratified epithelium. The Journal of Cell Biology. 159(2):325-336.*
Miller, G. (2002). Breaking down barriers. Science 297:1116-1118.*
Pettit et al. (1998). The development of site-specific drug-delivery systems for protein and peptide biopharmaceuticals. Trends Biotechnol 16: 343-349.*
Freedman et al. (1997). Linkage of a neurophysiological deficit in schizophrenia to a chromosome 15 locus. Proc. Natl. Acad. Sci. USA 94:587-592.*
Guan et al. (1999). Decreased protein level of nicotinic α7 subunit in the frontal cortex from schizophrenic brain. NeuroReoort. 10:1779-1782.*
Freedman et al. (1995). Evidence in postmortem brain tissue for decreased numbers of hippocampal nicotinic receptors in schizophrenia. Biol. Psychiatry. 38:22-33.*
Freedman et al. (2000). The α7-nicotinic acetylcholine receptor and the pathology of hippocampal interneurons in schizophrenia. Journal of Chemical Neuroanatomy. 20:299-306.*
Gault et al. (2003). Comparison of polymorphisms in the α7 nicotinic receptor gene and its partial duplication in schizophrenic and control subjects. American Journal of Medical Genetics Part B (Neuropsychiatric Genetics). 123B:39-49.*
Simosky et al. (2003). Clozapine improves deficient inhibitory auditory processing in DBA/2 mice, via a nicotinic cholinergic mechanism. Psychopharmacology. 165:386-396.*
Simosky et al. (2001). Intragastric DMXB-A, an α7 nicotinic agonist, improves deficient sensory inhibition of DBA/2 mice. Biol. Psychiatry. 50:493-500.*
Stevens et al. (1998). Selective α7-nicotinic agonists normalize inhibition of auditory response in DBA mice. Psychopharmacology. 136:320-327.*
O'Neill et al. (2003). DMXB, an α7 nicotinic agonist, normalizes auditory gating in isolation-reared rats. Psychopharmacology. 169:332-339.*
Grantham et al. (2003). Modulation of alpha 7 nicotinic receptors as a strategy for therapy in schizophrenia. Schizophrenia Research. 60(1), Suppl. 1:107.*
Martin et al. (2004). Alpha-7 nicotinic receptor agonists: potential new candidates for the treatment of schizophrenia. Psychopharmacology. 174:54-64.*
Adermann, et al., *Protein Sci.*, 8:810-819 (1999).
Blasi, et al., *Nat. Rev. Mol. Cell Biol.*, 3(12):932-943 (2002).
Borovikova, et al., *Nature*, 405:458-462 (2000).
Brakenhoff et al., *J. Cell Biol.*, 129(6):1677-1689 (1995).
Casey, et al., *Blood*, 84(4):1151-1156 (1994).
Chimienti, et al., *Hum. Mol. Genet.*, 12(22)3017-3024 (2003).
Eckl, et al., *Hum. Genet.*, 112:50-56 (2003).
Elias, et al., *J. Invest. Dermatol.*, 119:1128-1136 (2002).
Fischer, et al., *Eur. J. Hum. Genet.*, 6:542-547 (1998).
Fischer, et al., *Hum. Mol. Genet.*, 10(8):875-880 (2001).
Grando, et al., *J. Invest. Dermatol.*, 105:774-781 (1995).
Grando, et al., *Curr. Opin. Dermatol.*, 4:262-268 (1997).
Grando, S.A., *J. Invest. Dermatol. Symp. Proc.*, 2:41-48 (1997).
Horie, et al., *Genomics*, 53:365-368 (1998).
Ibenez-Tallon, et al., *Neuron*, 33(6):893-903 (2002).
Jacobi, et al., *Am. J. Pathol.*, 161(1):97-104 (2002).

(Continued)

*Primary Examiner*—Christine J. Saoud
*Assistant Examiner*—Jon M. Lockard
(74) *Attorney, Agent, or Firm*—Mintz, Levin, Cohn, Ferris, Glovsky and Popeo, P.C.; Ivor R. Elrifi; Christina K. Stock

(57) ABSTRACT

Disclosed herein are compositions and methods for the treatment or prevention of neurological disorders. Also disclosed are compositions and methods for the treatment or prevention of skin pathologies. The invention further discloses compositions and methods for the modulation of acetylcholine receptor activity. Antibodies generated against SLURP-1 and related proteins are also included.

7 Claims, 5 Drawing Sheets

OTHER PUBLICATIONS

Kini, R. M., *Clin. Exp. Pharmacol. Physiol.*, 29(9):815-822 (2002).
Köck, et al., *J. Exp. Med.*, 172:1609-1614 (1990).
Kondo, et al., *Eur. J. Immunol.*, 27:1713-1718 (1997).
Mastrangeli, et al., *Eur. J. Dermatol.*, 13(6):560-570 (2003).
Menon, et al., *J. Invest. Dermatol.*, 84(6):508-512 (1985).
Miwa, et al., *Neuron*, 23:105-114 (1999).
Montuori, et al., *J. Biol. Chem.*, 277(49):46932-46939 (2002).
Palfree, R. G. E., *Immunol. Today*, 12(5):170 (1991).
Ploug, et al., *J. Biol. Chem.*, 268(23):17539-17546 (1993).
Ploug, et al., *FEBS Lett.*, 349:163-168 (1994).
Reiter, et al., *Proc. Natl. Acad. Sci. USA*, 95:1735-1740 (1998).
Schrijvers, et al., *Exp. Cell Res.*, 196:264-269 (1991).
Shan, et al., *J. Immunol.*, 160:197-208 (1998).
Tone, et al., *J. Mol. Biol.*, 227:971-976 (1992).
Tsuji, et al., *Genomics*, 81:26-33 (2003).
Wang, et al., *Nature*, 421:384-388 (2003).
Ward, et al., *J. Invest. Dermatol.*, 120:96-98 (2003).

* cited by examiner

USE OF SLURP-1 COMPOSITIONS FOR TREATING SCHIZOPHRENIA

RELATED APPLICATIONS

This application claims priority to U.S. Ser. No. 60/463,418, filed Apr. 16, 2003, which is incorporated herein by reference in its entirety.

FIELD OF THE INVENTION

This invention relates generally to compositions and methods for the treatment or prevention of neurological disorders and skin pathologies as well as for the modulation of acetylcholine receptor activity.

BACKGROUND OF THE INVENTION

The Ly-6/uPAR superfamily of receptors and secreted proteins contains a carboxy-terminal consensus sequence motif CCXXXXCN (SEQ ID NO:1) and one or several repeats of the Ly-6/uPAR domain, which is defined by a distinct disulfide bonding pattern between eight or ten cysteine residues (See Ploug et al., J. Biol. Chem., 268, 17539–17546 (1993); Ploug and Ellis, FEBS Lett., 349, 163–168 (1994); Casey et al., Blood, 84, 1151–1156 (1994)).

The superfamily can be classified into two subfamilies on the basis of the presence or absence of a GPI-anchoring signal sequence (See Adermann et al., Protein Sci., 8, 810–819 (1999)). GPI-anchored Ly-6/uPAR receptor proteins include the retinoic acid-induced gene E (RIG-E, or human Ly-6E), the E48 antigen (human Ly-6D); Ly-6H; the PSCA; CD59 or protectin; Lynx1 and uPAR (See Shan et al., J. Immununol., 160, 197–208 (1998); Brakenhoff et al., J. Cell Biol., 129, 1677–1689 (1995); Horie et al., Genomics, 53, 365–368 (1998); Reiter et al., Proc. Natl Acad. Sci. USA, 95, 1735–1740 (1998); Tone et al., J. Mol. Biol., 227, 971–976 (1992)). The E48 gene is known to be expressed in human keratinocytes, but not in lymphocytes, and it modulates desmosomal cell-cell adhesion of keratinocytes (Brakenhoff et al., J. Cell Biol., 129, 1677–1689 (1995); Schrijvers et al., Exp. Cell. Res., 196, 264–269 (1991)). The urokinase-type plasminogen activator receptor (uPAR) interacts in dynamic association with integrins and initiates signaling events that alter cell adhesion, migration, proliferation and differentiation (See Blasi and Carmeliet, Nat. Rev. Mol. Cell. Biol., 3, 932–943 (2002)). uPAR is a distant Ly-6/uPAR family member and, contrary to other members, it contains three contiguous copies of the Ly-6/uPAR domain. Differential cleavage of these domains regulates the multiple functions of uPAR (See Palfree, Immunol. Today, 12, 170 (1991); Montuori, et al., J. Biol. Chem., 277, 46932–46939 (2002)).

The second subfamily, which has a Ly-6/uPAR domain but no GPI-anchoring signal sequence includes SLURP-1 and SLURP-2 (See Adermann et al., Protein Sci., 8, 810–819 (1999); Tsuji et al., Genomics, 81, 26–33 (2003)). Mutations in the gene encoding SLURP-1 have been implicated in Mal de Meleda (MdM), as the MdM gene is located in a cluster of Ly-6 genes on chromosome 8q24.3 (See Fischer et al., Eur. J. Hum. Genet., 6, 542–547 (1998); Fischer et al., Hum. Mol. Genet., 10, 875–880 (2001); Eckl et al, Hum. Genet., 112, 50–56 (2003); Ward et al., J. Invest. Dermatol., 120, 96–98 (2003)).

SUMMARY OF THE INVENTION

The present invention provides methods for treating a neurological disorder in a subject by administering an effective amount of SLURP-1 or a related protein to a subject suffering from the neurological disorder.

The present invention also provides methods for preventing or delaying the onset of a neurological disorder in a subject by administering an effective amount of SLURP-1 or a related protein to a subject at risk of developing or suffering from the neurological disorder.

Also provided are methods of providing neuroprotection to a subject by administering an effective amount of SLURP-1 or a related proteins to the subject where the neuroprotection prevents a neurological disorder caused by dysfunction of an acetylcholine receptor.

The present invention additionally provides methods for treating a skin pathology caused by dysfunction of an acetylcholine receptor expressed in the skin by administering an effective amount of SLURP-1 or a related protein to a subject suffering from the skin pathology.

The present invention also provides methods for preventing or delaying the onset of a skin pathology caused by dysfunction of an acetylcholine receptor expressed in the skin by administering an effective amount of SLURP-1 or a related protein to a subject at risk of developing or suffering from the skin pathology.

Also provided are compositions including an effective amount of SLURP-1, a SLURP-1 mimetic, or a combination thereof and a carrier, where the composition modulates the function of an alpha 7 nicotinic acetylcholine receptor or of a related protein. In one preferred embodiment, the composition is provided in a kit.

The invention also provides methods for modulating the activity of an acetylcholine receptor by contacting the acetylcholine receptor with an effective amount of SLURP-1, where the effective amount of SLURP-1 is from about 1.0 pM to about 10 μM. In one preferred embodiment, modulation of the acetylcholine receptor restores the proper function of the acetylcholine receptor.

The present invention further provides methods of screening for a modulator of acetylcholine receptor activity by a) exposing a first acetylcholine receptor with a candidate compound and measuring the activity of the first acetylcholine receptor following the exposure, b) exposing a second acetylcholine receptor with an effective amount of SLURP-1 or a related compound and measuring the activity of the second acetylcholine receptor following the exposure, and c) comparing the activity of the first acetylcholine receptor following the first exposure to the activity of the second acetylcholine receptor following the exposure with SLURP-1 or a related compound. In such methods, if the activity of the first acetylcholine receptor is similar to the activity of the second acetylcholine receptor, then the candidate compound is a modulator of acetylcholine receptor activity.

In preferred embodiments of the invention, the neurological disorder, that is treated and/or prevented, can be a pathology caused by dysfunction of an acetylcholine receptor. For example, the neurological disorder can include pain, neuropathic pain, schizophrenia, cognitive impairments, Alzheimer's disease, and Parkinson's disease. Likewise, the skin pathology, that is treated and/or prevented, can include Mal de Meleda, wound healing, and psoriasis.

In a preferred embodiments of the invention, the acetylcholine receptor is a nicotinic acetylcholine receptor. Specifically, the nicotinic acetylcholine receptor can be an alpha 7 nicotinic acetylcholine receptor or an alpha 7 nicotinic acetylcholine receptor-related protein.

In some embodiments, SLURP-1 is administered to the subject in a mature form. As used herein, the mature form of SLURP-1 includes amino acids 23–103 of SLURP-1.

The present invention also provides methods of treating a neurological disorder caused by the dysfunction of the alpha 7 nicotinic acetylcholine receptor by administering a composition containing an effective amount of SLURP-1, or SLURP-1 mimetic or a combination thereof and a carrier to a subject suffering from the neurological disorder.

Also provided are methods of preventing or delaying the onset of a neurological disorder caused by the dysfunction of the alpha 7 nicotinic acetylcholine receptor by administering a composition of the present invention to a subject at risk of developing or suffering from the neurological disorder.

The present invention further provides methods of treating a skin pathology caused by the dysfunction of an alpha 7 nicotinic acetylcholine receptor expressed in the skin by administering a composition containing an effective amount of SLURP-1, or SLURP-1 mimetic or a combination thereof and a carrier to a subject suffering from the skin pathology.

Likewise, the present invention also provides methods of preventing or delaying the onset of a skin pathology caused by the dysfunction of an alpha 7 nicotinic acetylcholine receptor expressed in the skin by administering a composition of the present invention to a subject at risk of developing or suffering from the skin pathology.

The present invention provides a antibody with high specific binding affinity to SLURP-1. The antibodies of the invention can be monoclonal, polyclonal or humanized.

In various embodiments of the invention, an effective amount of SLURP-1 can be from about 1.0 pM to about 10 μM or form a solution contacting the acetylcholine receptor at about 1.0 pM to about 10 μM. The effective amount of SLURP-1 can be administered orally, intravenously, intraperitoneally, intranasally, or intramuscularly. Administration of SLURP-1 can also include the administering an expression vector capable of expressing the SLURP-1 protein into the subject. Preferably, the subject receiving SLURP-1 is a mammal. More preferably, the subject is a human.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other features and advantages of the invention will be apparent from the following detailed description and claims.

DETAILED DESCRIPTION OF THE INVENTION

Figure 1:
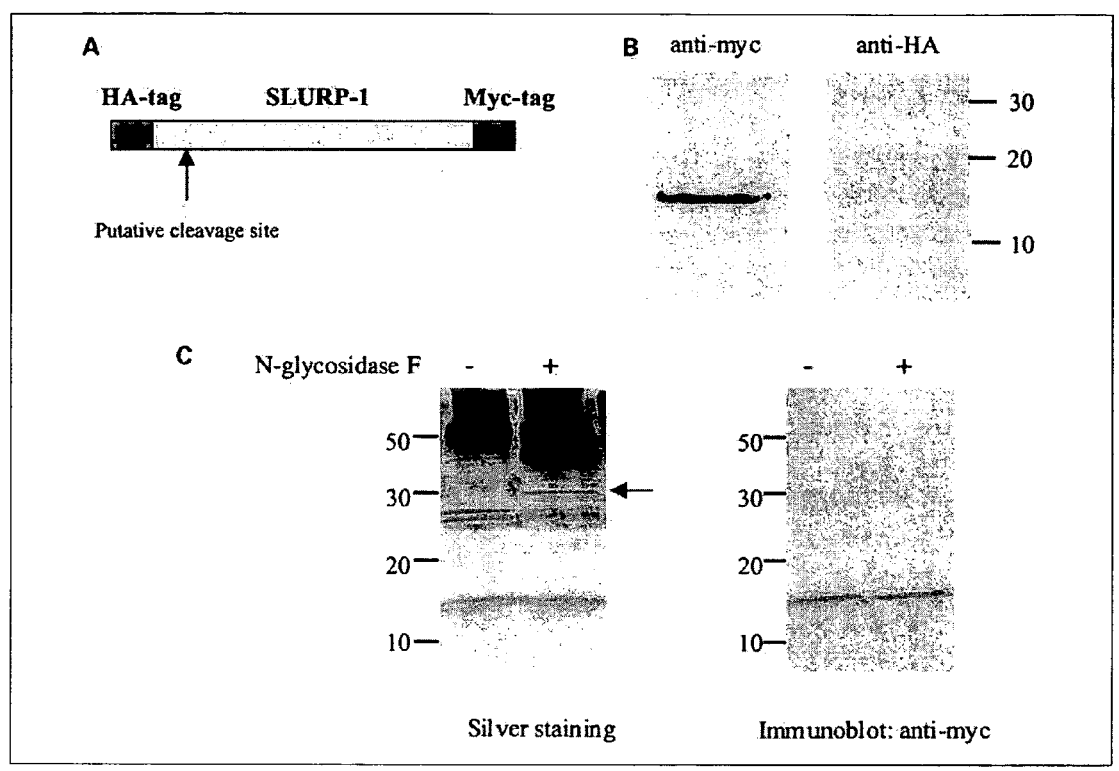
FIG. 1A is a schematic of a recombinant SLURP-1 construct tagged with HA-tag and myc-tag
FIGS. 1B and 1C are corresponding photographs of immunoblots showing that the signal sequence of SLURP-1 is cleaved during processing and showing that SLURP-1 is not glycosylated, respectively.

The present invention is based in part on the ability of SLURP-1 to modulate acetylcholine receptor activity. SLURP-1 is a 9 kDa protein encoded by the ARS B gene. The amino acid sequence of SLURP-1 has 103 amino acid residues:

(SEQ ID NO:2)
MASRWAVQLLLVAAWSMGCGEALKCYTCKEPMTSASCRTITRCKPEDTAC

MTTLVTVEAEYPFNQSPVVTRSCSSSCVATDPDSIGAAHLIFCCFRDLCN

SEL.

The present invention provides methods of treating, preventing or delaying the onset of a neurological disorder or a skin pathology as well as methods of modulating the activity of an acetylcholine receptor. As described herein in Examples 1 and 2 infra, SLURP-1 contains a signal peptide at amino acids 1–22 and is secreted by N-terminal signal cleavage in a non-glycosylated, mature form (amino acids 23–103 of SEQ ID NO:2).

SLURP-1 has been shown herein to interact with acetylcholine receptors and modulates their activity. For example, SLURP-1 enhanced the amplitude of the acetylcholine-evoked macroscopic currents in a concentration-dependent manner. Specifically, SLURP-1 (at a concentration of 200 pM) increased the amplitude of the acetylcholine-evoked macroscopic currents by 421±130% (n=6), and 20 nM SLURP-1 enhanced the amplitude by 1214±550% (n=4). See, Example 4, infra. Moreover, SLURP-1 induced an increase in both current amplitude and sensitivity to acetylcholine as well as an increase in the Hill coefficient. Because the application of SLURP-1 did not evoke currents in the absence of acetylcholine, SLURP-1 does not function as a ligand or as a neurotransmitter. Rather, SLURP-1 modulates acetylcholine receptor function in the presence of its natural ligand, which demonstrates that SLURP-1 acts as a positive allosteric effector at acetylcholine receptors. This finding is further supported by the increased acetylcholine sensitivity and increased apparent cooperativity that are hallmarks of allosteric effectors (See Changeux and Edelstein, Curr. Opin. Neurobiol., 11, 369–377 (2001)).

The present invention also includes methods of modulating epidermal calcium homeostasis and keratinocyte proliferation and differentiation. SLURP-1 is closely related to the subfamily of single-domain snake and frog cytotoxins, i.e. a-bungarotoxin (Bgtx) and a-cobratoxin (Cbtx). See, Example 3, infra. This high degree of structural homology between SLURP-1 and these snake neurotoxins indicates that SLURP-1 likely interacts with ion channels, the muscle and neuronal subtypes of the nicotinic acetylcholine receptor, and both muscarinic and nicotinic acetylcholine receptors that are expressed in keratinocytes (See Grando and Horton, Curr. Opin. Dermatol., 4, 262–268 (1997); Grando, J. Invest. Dermatol. Symp. Proc., 2, 41–48 (1997)). Epidermal nicotinic acetylcholine receptors are involved in regulating cell adhesion, motility of epidermal keratinocytes and wound healing (See et al., J. Invest. Dermatol., 105, 774–781 (1995); Jacobi et al., Am. J. Pathol., 161, 97–104 (2002)).

These SLURP-1 interactions are comparable to the action of Lynx1. Lynx1 has been shown to interact with neuronal nicotinic acetylcholine receptors in the central nervous system where it modulates the cellular calcium permeability (See Miwa et al., Neuron, 23, 105–114 (1999)). Calcium has an established role in the homeostasis of mammalian skin and modulates keratinocyte proliferation and differentiation (See Menon et al., J. Invest. Dermatol., 84, 508–512 (1985); Elias et al., J. Invest. Dermatol., 119, 1128–1136 (2002)). Moreover, the association between the keratotic palmoplantar skin disorder, Mal de Meleda, and mutations in SLURP-1 indicate that alteration or mutation of secreted SLURP-1 protein can also disrupt skin homeostasis. Further, acetylcholine signaling through alpha (a7) nicotinic acetylcholine receptor channels appears to be functional in keratinocytes and essential for epidermal homeostasis.

The present invention also provides methods of modulating inflammatory responses (e.g., cutaneous inflammation). For example, TNF-a is a pleiotropic proinflammatory cytokine that elicits a large number of biological effects, including inflammatory and immunoregulatory responses (See Kondo and Sauder, Eur. J. Immunol., 27, 1713–1718 (1997)). TNF-a is known to be released from keratinocytes after stimulation with lipopolysaccharide (LPS), ultraviolet (UV) light or wound healing and participates in cutaneous inflammation (See Kock et al., J. Exp. Med., 172, 1609–1614 (1990)). Acetylcholine inhibits the release of TNF-a and other cytokines on primary macrophages, through a mechanism dependent on bungarotoxin-sensitive receptors (See Borovikova et al., Nature, 405, 458–462 (2000)). Moreover, the a7 nicotinic acetylcholine receptor subunit is required for inhibition of TNF-a release by macrophages (See Wang et al., Nature, 421, 384–388 (2003)), and inactivation of this pathway can contribute to excessive systemic release of cytokines during endotoxaemia or other injury. Further, as Mal de Meleda is characterized by a clinical phenotype with marked cutaneous inflammation and is due to absent or mutated SLURP-1, it is likely that SLURP-1 controls TNF-a release in dermal macrophages and in keratinocytes by activation of nicotinic acetylcholine receptors, thereby reducing inflammation. Thus, SLURP-1 or alterations thereof (e.g., point mutations, deletions, etc.) can modify the secretion of TNF-a from macrophages and can modify inflammatory responses.

The high degree of structural homology between SLURP-1 and the three-fingered protein family combined with the ability of SLURP-1 to modulate acetylcholine receptor activity, indicates that SLURP-1 is also functionally homologous to the venom toxins. Thus, it is useful for treating or preventing neurological disorders or skin pathologies, modulating epidermal calcium homeostasis and keratinocyte proliferation and differentiation, modulating the secretion of TNF-a and modulating inflammatory responses.

Methods of Using SLURP-1 as a Neuromodulator

The present invention provides methods for treating neurological disorders in a subject by administering an effective amount of SLURP-1 or a SLURP-1 related protein to the subject suffering from the neurological disorder.

Also provided by, the present invention are methods for preventing or delaying the onset of neurological disorders in a subject by administering an effective amount of SLURP-1 or a related protein to the subject suffering from the neurological disorder.

The present invention further provides methods of providing neuroprotection to a subject by administering an effective amount of SLURP-1 or a related protein to the subject where the neuroprotection prevents a neurological disorder caused by dysfunction of an acetylcholine receptor.

For example, the neurological disorder can include any a pathology caused by dysfunction of an acetylcholine receptor. Such disorders include, but are not limited to pain, neuropathic pain, schizophrenia, cognitive impairments, Alzheimer's disease, and Parkinson's disease. In one preferred embodiment, the acetylcholine receptor is a nicotinic acetylcholine receptor or a muscarinic acetylcholine receptor. Preferably, the nicotinic acetylcholine receptor is an alpha 7 ($\alpha$7) nicotinic acetylcholine receptor or an alpha 7 nicotinic acetylcholine receptor related protein.

In the methods and compositions of the invention, SLURP-1 has the amino acid sequence of SEQ ID NO:2. In a preferred embodiment, SLURP-1 is in a mature form. More preferably, the mature form of SLURP-1 includes amino acids 23–103 of SLURP-1.

The terms "subject" or "patient" are well-recognized in the art, and, are used interchangeably herein to refer to a mammal, including dog, cat, rat, mouse, monkey, cow, horse, goat, sheep, pig, camel, and, most preferably, a human. In some embodiments, the subject is a subject in need of treatment. However, in other embodiments, the subject can be a normal subject, e.g., a subject having no known or diagnosed neurological disorder, e.g., a neurological disorder-free subject. Alternatively, the subject has a known, diagnosed, or suspected neurological disorder.

The terms "treating" or "preventing" are also art-recognized. As used herein, there terms refer to inhibiting, reducing, ameliorating, or curing a condition (such as a neurological disorder) for which such treatment is indicated. The progress of such treatment can be monitored, e.g., by any measures known in the art.

A compound or pharmaceutical composition of the invention (e.g., SLURP-1, a SLURP-1 related protein, or any member of the secreted Ly-6/uPAR family) can be administered to a subject in many of the well-known methods currently used for the treatment of neurological disorders. For example, for treatment of neurological disorders, a compound of the invention can be administered orally, intravenously, intraperitoneally, intranasally, or intramuscularly. The dose chosen should be sufficient to constitute effective treatment but not so high as to cause unacceptable side effects. The state of the disease condition (e.g., the neurological disorder) and the health of the subject/patient should preferably be closely monitored during and for a reasonable period after administration. Administration can also include the administration of an expression vector capable of expressing the SLURP-1 protein, the SLURP-1 related protein, or a member of the secreted Ly-6/uPAR family into the subject/patient. Preferably, members of the secreted Ly-6/uPAR family include but are not limited to, Lynx-1 Isoform A, Lynx-1 Isoform B (SLURP-2) and RGTR-430.

The term "effective amount" well known in the art used herein. As it refers to an amount effective to achieve a desired result, such as preventing, treating, inhibiting, reducing, ameliorating, or curing. In one embodiment, a compound or pharmaceutical composition of the invention (e.g., SLURP-1, SLURP-1 related protein, or a member of the secreted Ly-6/uPAR family) is administered in an effective amount of about 1.0 pM to about 10 μM. In other embodiments, the effective amount is about 10 pM to about 1 μM; about 1 pM to about 100 nM; preferably about 10 pM to about 10 nM; or more preferably about 100 pM to about 1 nM.

As used herein a "SLURP-1 related protein" is a protein that displays structural homology to SLURP-1 (SEQ ID NO:2) or a mature form of SLURP-1 (e.g., amino acids 23–103 of SEQ ID NO:2). In one embodiment, a SLURP-1 related protein is about 75% homologous/identical to SLURP-1 or a mature form of SLURP-1. In other embodiments, a SLURP-1 related protein is about 80% homologous/identical; about 85% homologous/identical; preferably about 90% homologous/identical; more preferably about 95% homologous/identical or most preferably about 99% homologous/identical. In a preferred embodiment, a SLURP-1 related protein functional homologous to SLURP-1 or a mature form of SLURP-1. A SLURP-1 related protein can include but is not limited to members of the secreted Ly-6/uPAR family (e.g., Lynx-1 Isoform A, Lynx-1 Isoform B (SLURP-2), RGTR-430, etc.)

Homology/Identity is typically measured using sequence analysis software (e.g., Sequence Analysis Software Package of the Genetics Computer Group, University of Wisconsin Biotechnology Center, 1710 University Avenue, Madison, Wis. 53705). Similar amino acid sequences are aligned to obtain the maximum degree of homology (i.e., identity). To this end, it may be necessary to artificially introduce gaps into the sequence. Once the optimal alignment has been set up, the degree of homology (i.e., identity) is established by recording all of the positions in which the amino acids of both sequences are identical, relative to the total number of positions.

Similarity factors include similar size, shape and electrical charge. One particularly preferred method of determining amino acid similarities is the PAM250 matrix described in Dayhoff et al., 5 Atlas Of Protein Sequence And Structure 345–352 (1978 & Suppl.), incorporated by reference herein. A similarity score is first calculated as the sum of the aligned pairwise amino acid similarity scores. Insertions and deletions are ignored for the purposes of percent homology and identity. Accordingly, gap penalties are not used in this calculation. The raw score is then normalized by dividing it by the geometric mean of the scores of the candidate compound and the reference sequence. The geometric mean is the square root of the product of these scores. The normalized raw score is the percent homology.

Methods of Using SLURP-1 to Treat or Prevent Skin Pathologies

The present invention additionally provides methods for treating skin pathologies caused by dysfunction of an acetylcholine receptor expressed in the skin by administering an effective amount of SLURP-1 or a SLURP-1 related protein to a subject suffering from the skin pathology.

Moreover, the present invention also provides methods for preventing or delaying the onset of skin pathologies caused by dysfunction of an acetylcholine receptor expressed in the skin by administering an effective amount of SLURP-1 or a SLURP-1 related protein to a subject at risk of developing or suffering from the skin pathology.

Also provided herein are methods for modulating epidermal calcium homeostasis by contacting the acetylcholine receptor with an effective amount of SLURP-1, where the effective amount of SLURP-1 is from about 1 pM to about 10 μM.

The present invention further provides methods for modulating keratinocyte proliferation and differentiation by contacting the acetylcholine receptor with an effective amount of SLURP-1 or a SLURP-1 related protein, where the effective amount is from about 1 pM to about 10 μM.

The invention also provides methods for modulating the secretion of TNF-a by contacting the acetylcholine receptor with an effective amount of SLURP-1 or a SLURP-1 related protein, where the effective amount is from about 1 pM to about 10 μM.

Moreover, the invention also provides methods for modulating an inflammatory response by contacting the acetylcholine receptor with an effective amount of SLURP-1 or a SLURP-1 related protein, where the effective amount of SLURP-1 is from about 1 pM to about 10 μM.

Preferably, the acetylcholine receptor is a nicotinic acetylcholine receptor or a muscarinic acetylcholine receptor. For example, the nicotinic acetylcholine receptor is an alpha 7 nicotinic acetylcholine receptor or an alpha 7 nicotinic acetylcholine receptor related protein.

In one embodiment, SLURP-1 that is administered to the subject has the amino acid sequence of SEQ ID NO:2. In one preferred embodiment, SLURP-1 is in a mature form. Those skilled in the art will recognize that the mature form of SLURP-1 includes amino acids 23–103 of SEQ ID NO:2.

Preferably, the subject is a mammal. More preferably, the subject is a human. The subject may be a subject in need of treatment, or the subject can be a normal subject, e.g., a subject having no known or diagnosed skin pathologies, e.g., a skin pathology-free subject. In other embodiments, the subject has a known, diagnosed, or suspected skin pathology. The skin pathology may include but is not limited to, Mal de Meleda, wound healing or psoriasis. Those skilled in the art will recognize that the methods and compositions disclosed herein can be used to treat or prevent any skin pathology resulting from a dysfunction of an acetylcholine receptor expressed in the skin.

A compound or pharmaceutical composition of the invention (e.g., SLURP-1, a SLURP-1 related protein, or a member of the secreted Ly-6/uPAR family) can be administered to a subject in many of the well-known methods currently used for treatment of skin pathologies. For example, for treatment of skin pathologies, a compound of the invention can be administered orally, intravenously, intraperitoneally, intranasally, or intramuscularly. The dose chosen should be sufficient to constitute effective treatment but not so high as to cause unacceptable side effects. Selection of an appropriate dose is within the skill of those in the art. The state of the disease condition (e.g., the skin pathology) and the health of the subject/patient should preferably be closely monitored during and for a reasonable period after administration. Administration can also include the administration of an expression vector capable of expressing the SLURP-1 protein, SLURP-1 related protein, or a member of the secreted Ly-6/uPAR family into the subject/patient. Suitable members of the secreted Ly-6/uPAR family include, but are not limited to, Lynx-1 Isoform A, Lynx-1 Isoform B (SLURP-2) and RGTR-430.

For example, a compound or pharmaceutical composition of the invention (e.g., SLURP-1, SLURP-1 related protein, or a member of the secreted Ly-6/uPAR family) is administered in an effective amount of about 1.0 pM to about 10 μM. In other embodiments, the effective amount is about 10 pM to about 1 µM; about 1 pM to about 100 Mn; preferably about 10 pM to about 10 nM; or a more preferably about 100 pM to about 1 nM.

Compositions of SLURP-1 to Treat or Prevent Neurological Disorders or Skin Pathologies The present invention also provides compositions including an effective amount of SLURP-1, a SLURP-1 mimetic, a SLURP-1 related protein, or a combination thereof and a carrier, where the composition modulates the function of an alpha 7 nicotinic acetylcholine receptor or of a related protein. In one preferred embodiment, the composition is provided as part of a kit.

Likewise, the present invention also provides methods of treating a neurological disorder caused by the dysfunction of the alpha 7 nicotinic acetylcholine receptor by administering a composition of the present invention to the subject suffering from the neurological disorder.

Also provided are methods of preventing or delaying the onset of a neurological disorder caused by the dysfunction of the alpha 7 nicotinic acetylcholine receptor by administering a composition of the present invention to the subject at risk of developing or suffering from the neurological disorder.

The present invention further provides a method of treating a skin pathology caused by the dysfunction of an alpha 7 nicotinic acetylcholine receptor expressed in the skin by administering a composition of the present invention to the subject suffering from the skin pathology.

Moreover, the present invention also provides a method of preventing or delaying the onset of a skin pathology caused by the dysfunction of an alpha 7 nicotinic acetylcholine receptor expressed in the skin by administering a composition of the present invention to the subject at risk of developing or suffering from the skin pathology.

The methods and compositions present invention also encompass SLURP-1 peptide mimetics (peptidomimetics) SLURP-1 related protein peptide mimetics, and peptide mimetics of members of the secreted Ly-6/uPAR family. Techniques for development of peptide mimetics are well known in the art. (See for example, Navia and Peattie, Trends Pharm Sci 14: 189–195, 1993; Olson et al, J Med Chem 36: 3039–3049 which are incorporated by reference). Specifically using the amino acid sequence of SLURP-1, or SLURP-1 related protein, or members of the secreted Ly-6/uPAR family, X-ray crystallography and nuclear magnetic resonance technology along with computerized molecular modeling, a pharmacophore hypothesis is developed and peptide mimetic compounds are made and tested in an assay system.

For example, the invention includes compounds or compositions of the invention (e.g., SLURP-1 or a member of the secreted Ly-6/uPAR family in which one or more peptide bonds have been replaced with an alternative type of covalent bond (a "peptide mimetic"), which is not susceptible to cleavage by peptidases. Where proteolytic degradation of the peptides following injection into the subject is a problem, replacement of a particularly sensitive peptide bond with a noncleavable peptide mimetic renders the resulting peptide more stable and thus more useful as a therapeutic. Such mimetics, and methods of incorporating them into peptides, are well known in the art. Similarly, the replacement of an L-amino acid residue is a standard way of rendering the peptide less sensitive to proteolysis. The molecular interactions of a peptide mimetic are similar to that of the naturally-occurring molecule.

The compounds, compositions or pharmaceutical compositions of the invention (e.g., SLURP-1, SLURP-1 related protein, or a member of the secreted Ly-6/uPAR family), and derivatives, fragments, analogs and homologs thereof, can be incorporated into compositions suitable for administration. Such compositions typically comprise the nucleic acid molecule, or protein, and a pharmaceutically acceptable carrier. As used herein, "carrier" or "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be acetylcholineieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating a compound or pharmaceutical composition of the invention (e.g., SLURP-1, a SLURP-1 related protein, or a member of the secreted Ly-6/uPAR family) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811, which is incorporated herein by reference in its entirety.

It is especially advantageous to formulate oral or parenteral compositions in dosage unit form for ease of administration and uniformity of dosage. Dosage unit form, as used herein, refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

The compositions of the invention can be included in a kit, container, pack, or dispenser together with instructions for administration.

Another aspect of the invention pertains to vectors, preferably expression vectors, containing a nucleic acid encoding an SLURP-1 protein, a SLURP-1 related protein, or a protein from any member of the secreted Ly-6/uPAR family, or derivatives, fragments, analogs or homologs thereof. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention can be designed for expression of a SLURP-1 protein, a SLURP-1 related protein, or a protein from any member of the secreted Ly-6/uPAR family in prokaryotic or eukaryotic cells. For example, the proteins can be expressed in bacterial cells such as *Escherichia coli*, insect cells (using baculovirus expression vectors) yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Methods of Using SLURP-1 to Modulate Acetylcholine Receptor Activity

The present invention also provides methods for modulating the activity of an acetylcholine receptor by contacting the acetylcholine receptor with an effective amount of SLURP-1 or a SLURP-1 related protein, where the effective amount is from about 1 pM to about 10 µM. In a preferred embodiment, modulation of the acetylcholine receptor restores the proper function of the acetylcholine receptor.

For example, the acetylcholine receptor is a nicotinic acetylcholine receptor or a muscarinic acetylcholine receptor. Preferably, the nicotinic acetylcholine receptor is an alpha 7 nicotinic acetylcholine receptor or an alpha 7 nicotinic acetylcholine receptor-related protein.

SLURP-1 has the amino acid sequence of SEQ ID NO:2. In one preferred embodiment, SLURP-1 is in a mature form. More preferably, the mature form of SLURP-1 includes amino acids 23–103 of SEQ ID NO:2.

The terms "modulate" or "modulating" are art-recognized. As used herein, thus refer to stimulating, inducing, upregulating, enhancing or decreasing, inhibiting, reducing, repressing. As used herein, a "modulator" is a molecule which stimulates (i.e. induces, enhances or upregulates) or inhibits (i.e. reduces, represses or decreases) the activity of an acetylcholine receptor.

Methods of Screening for Acetylcholine Receptor Activity Modulators

The present invention additionally provides a method of screening for a modulator of acetylcholine receptor activity by a) exposing a first acetylcholine receptor with a candidate compound and measuring the activity of the first acetylcholine receptor following the exposure, b) exposing a second acetylcholine receptor with an effective amount of SLURP-1 or a related compound and measuring the activity of the second acetylcholine receptor following the exposure, and c) comparing the activity of the first acetylcholine receptor following the first exposure to the activity of the second acetylcholine receptor following the exposure with SLURP-1 or a related compound. If the activity of the first acetylcholine receptor is similar to the activity of the second acetylcholine receptor following exposure, then the candidate compound is a modulator of acetylcholine receptor activity.

In one embodiment, the acetylcholine receptor is a nicotinic acetylcholine receptor or a muscarinic acetylcholine receptor. Preferably, the nicotinic acetylcholine receptor is an alpha 7 nicotinic acetylcholine receptor or an alpha 7 nicotinic acetylcholine receptor related protein.

SLURP-1 has the amino acid sequence of SEQ ID NO:2. In one preferred embodiment, SLURP-1 is in a mature form. The mature form of SLURP-1 includes amino acids 23–103 of SEQ ID NO:2.

Typically, a compound of the invention (e.g., SLURP-1, a SLURP-1 related protein, or a member of the secreted Ly-6/uPAR family) forms a solution for contacting the acetylcholine receptor in an effective amount of about 1.0 pM to about 10 µM. In other embodiments, the effective amount is about 10 pM to about 1 µM; about 1 pM to about 100 nM; preferably 10 pM to about 10 nM; or more preferably 100 pM to about 1 nM.

Anti-SLURP Antibodies

Also provided by the present invention are antibodies having high specific binding affinity to SLURP-1. The antibody can be, e.g., monoclonal, polyclonal or humanized. For example, high specific binding affinity may be represented by a dissociation constant less than $5.0 \times 10^{-5}$ M. Preferably, the high specific binding affinity is represented by a dissociation constant less than $5.0 \times 10^{-7}$ M. More preferably, the high specific binding affinity is represented by a dissociation constant less than $5.0 \times 10^{-9}$ M.

The term "antibody" as used herein refers to immunoglobulin molecules and immunologically active portions of immunoglobulin (Ig) molecules, i.e., molecules that contain an antigen binding site that specifically binds (immunoreacts with) an antigen. Such antibodies include, but are not limited to, polyclonal, monoclonal, chimeric, single chain, $F_{ab}$, $F_{ab'}$ and $F_{(ab')2}$ fragments, and an $F_{ab}$ expression library. In general, an antibody molecule obtained from humans relates to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain. Reference herein to antibodies includes a reference to all such classes, subclasses and types of human antibody species.

An isolated SLURP-1 protein, SLURP-1 related protein, or SLURP-1 peptide mimetic of the invention can serve as an antigen, or a portion or fragment thereof, and additionally can be used as an immunogen to generate antibodies that immunospecifically bind the antigen, using standard techniques for polyclonal and monoclonal antibody preparation. The full-length protein can be used or, alternatively, the invention provides antigenic peptide fragments of the antigen for use as immunogens. An antigenic peptide fragment comprises at least 6 amino acid residues of the amino acid sequence of the full length protein, and encompasses an epitope thereof such that an antibody raised against the peptide forms a specific immune complex with the full length protein or with any fragment that contains the epitope. By epitope, reference is made to an antigenic determinant of a polypeptide. Typically, epitopes contain hydrophilic amino acids such that the particular region of the polypeptide is located on its surface and likely to be exposed in an aqueous based milieu. Preferably, the antigenic peptide comprises at least 3 amino acid residues in a spatial conformation which is unique to the epitope. Generally, the antigenic peptide comprises at least 5 amino acid residues, or at least 10 amino acid residues, or at least 15 amino acid residues, or at least 20 amino acid residues, or at least 30 amino acid residues. Furthermore, antibodies to a SLURP-1 protein, SLURP-1 related protein, or SLURP-1 peptide mimetic or fragments thereof can also be raised against oligopeptides that include a conserved region.

Hydrophobicity analysis of a SLURP-1 protein, SLURP-1 related protein, or SLURP-1 peptide mimetic sequence will indicate which regions are particularly hydrophilic and, therefore, are likely to encode surface residues useful for targeting antibody production. As a means for targeting antibody production, hydropathy plots showing regions of hydrophilicity and hydrophobicity may be generated by any method well known in the art, including, for example, the Kyte Doolittle or the Hopp Woods methods, either with or without Fourier transformation. See, e.g., Hopp and Woods, 1981, Proc. Nat. Acad. Sci. USA 78: 3824–3828; Kyte and Doolittle 1982, J. Mol. Biol. 157: 105–142, each of which is incorporated herein by reference in its entirety. Antibodies that are specific for one or more domains within an antigenic protein, or derivatives, fragments, analogs or homologs thereof, are also provided herein. A protein of the invention, or a derivative, fragment, analog, homolog or ortholog thereof, may be utilized as an immunogen in the generation of antibodies that immunospecifically bind these protein components.

Various procedures known within the art may be used for the production of polyclonal or monoclonal antibodies directed against a protein of the invention, or against derivatives, fragments, analogs homologs or orthologs thereof (See for example, Antibodies: A Laboratory Manual, Harlow E, and Lane D, 1988, Cold Spring Harbor Laboratory Press, Cold Spring Harbor, N.Y., incorporated herein by reference). Some of these antibodies are discussed below.

For the production of polyclonal antibodies, various suitable host animals (e.g., rabbit, goat, mouse or other mammal) may be immunized by one or more injections with the native protein, a synthetic variant thereof, or a derivative of the foregoing. An appropriate immunogenic preparation can contain, for example, the naturally occurring immunogenic protein, a chemically synthesized polypeptide representing the immunogenic protein, or a recombinantly expressed immunogenic protein. Furthermore, the protein may be conjugated to a second protein known to be immunogenic in the mammal being immunized. Examples of such immunogenic proteins include but are not limited to keyhole limpet hemocyanin, serum albumin, bovine thyroglobulin, and soybean trypsin inhibitor. The preparation can further include an adjuvant. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), adjuvants usable in humans such as Bacille Calmette-Guerin and *Corynebacterium parvum*, or similar immunostimulatory agents. Additional examples of adjuvants which can be employed include MPL-TDM adjuvant (monophosphoryl Lipid A, synthetic trehalose dicorynomycolate) and CpG dinucleotide motifs (See, Krieg, A. M. Biochim Biophys Acta 1489(1):107–16, 1999). The polyclonal antibody molecules directed against the immunogenic protein can be isolated from the mammal (e.g., from the blood) and further purified by well known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25–28).

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs thus contain an antigen binding site capable of immunoreacting with a particular epitope of the antigen characterized by a unique binding affinity for it. Monoclonal antibodies can be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (U.S. Pat. No. 4,816,567; Morrison, Nature 368, 812–13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies directed against the protein antigens of the invention can further comprise humanized antibodies or human antibodies. These antibodies are suitable for administration to humans without engendering an immune response by the human against the administered immunoglobulin. Humanized forms of antibodies are chimeric immunoglobulins, immunoglobulin chains or fragments thereof (such as Fv, Fab, Fab', F(ab')$_2$ or other antigen-binding subsequences of antibodies) that are principally comprised of the sequence of a human immunoglobulin, and contain minimal sequence derived from a non-human immunoglobulin. Humanization can be performed following the method of Winter and co-workers (See, Jones et al., Nature, 321:522–525 (1986); Riechmann et al., Nature, 332:323–327 (1988); Verhoeyen et al., Science, 239:1534–1536 (1988)), by substituting rodent CDRs or CDR sequences for the corresponding sequences of a human antibody. (See also U.S. Pat. No. 5,225,539.) The humanized antibody optimally also will comprise at least a portion of an immunoglobulin constant region (Fc), typically that of a human immunoglobulin (See, Jones et al., 1986; Riechmann et al., 1988; and Presta, Curr. Op. Struct. Biol., 2:593–596 (1992)).

The invention will be further described in the following examples, which do not limit the scope of the invention described in the claims.

EXAMPLES

Example 1

To assess whether SLURP-1 is a secreted peptide and to determine the presence of a putative cleavage site of the signal sequence, a recombinant protein SLURP-1 with an N-terminal haemaglutinin (HA) tag and a C-terminal myc tag was produced. Specifically, plasmids were constructed. Specifically, for expression in mammalian cells, the cDNA encoding for SLURP-1 was modified by PCR to add 5'HindIII and 3'XbaI restriction sites at their termini with the following primers:

```
sense,      5'-AAGCTTGGAGCAATGGCCTCTCGCTGG       (SEQ ID NO:3)
and antisense,  5'-TCTAGAGAGTTCCGAGTTGCAGAGGTC.      (SEQ ID NO:4)
```

The PCR fragments were purified from agarose gels and ligated into HindIII- and XbaI-digested pBudCE4 (Invitrogen) to give the plasmid pBud-SLURP-1, which allowed addition of a C terminal myc tag for detection by western analysis and $His_6$ tag for purification. To generate the recombinant SLURP-1 protein with tags at both N- and C-termini, the cDNA encoding for SLURP-1 was amplified from pBud-SLURP-1 by PCR using primers containing 5'EcoRV and 3'BglII restriction sites at their termini and including the myc tag. The following primers were used:

```
sense,      5'-GAGATATCGGAGCAATGGCC-TCTCG                    (SEQ ID NO:5)
and antisense,  5'-AGAGATCTTCACAGATCCTCTT-CTGAGATG AGTTT.       (SEQ ID NO:6)
```

The PCR fragments were purified from agarose gels and ligated into EcoRV- and BglII-digested pCRUZ-HA (Santa Cruz), to generate pCSLURP-1, which allowed addition of an N-terminal haemagglutinin (HA) tag.

The resulting plasmids were then used to transform competent XL1-Blue cells. Single colonies were picked, and plasmid DNA was isolated and purified using reagents from Qiagen according to the manufacturer's instructions. For expression in insect cells, the pBud-SLURP-1 plasmid was digested by HindIII and EcoRV. The fragment corresponding to SLURP-1 cDNA with a myc tag at C-terminus was purified from agarose gels and ligated into HindIII- and XbaI-digested pIZ (Invitrogen), thus generating pIZ-SLURP-1, which encodes for the same protein as pBud-SLURP-1, including myc and $His_6$ tags. Correct insertion and in frame cloning of all plasmids was verified by sequencing.

HEK 293T cells (ATCC CRL-11268) were cultured in Dulbecco's modified Eagle's medium supplemented with 10% fetal calf serum (Gibco), 2 mM L-glutamine, 100 units/ml penicillin, and 100 mg/ml streptomycin, at 37° C. in a 5% $CO_2$ humidified atmosphere. The cells were harvested by trypsinization when ~90% confluent and plated at split ratios of 1:5. Stable cell lines expressing SLURP-1 were generated by calcium phosphate transfection of pBud-SLURP-1 as previously described (See, Jordan et al., Nucl. Acids Res., 24, 596–601 (1996)) and Zeocin selection. Clonal cell lines were isolated by the dilution method. Trichoplusia ni (HighFive, Invitrogen) cells were maintained at 27° C. in Express Five® SFM medium (Life Technologies). To generate stable cell lines, 10 μg of pIZ-SLURP-1 was transfected in HighFive cells with Cellfectin™ according to the manufacturer's instructions. Zeocin was added 48 h later for selection. Clonal cell lines were isolated with cloning cylinders.

The produced recombinant protein SLURP-1 with an N-terminal haemaglutinin (HA) tag and a C-terminal myc tag is shown in FIG. 1A. Following transient transfection of 293T cells with the construct, SLURP-1 was identified 48 h later in the culture medium by immunoblotting with anti-myc antibodies (See, FIG. 1B). As shown in FIG. 1B, immunoblotting with anti-HA antibodies did not indicate the presence of SLURP-1 in the culture medium. These result show that the signal sequence of SLURP-1 is cleaved before secretion during intracellular processing.

Recombinant polyhistidine-tagged SLURP-1 was purified by a cobalt affinity chromatography with Talon resin (Clontech). Specifically, recombinant SLURP-1 was purified using the $His_6$ tag from the culture medium of stably transfected mammalian and insect cells, which were cultured for 3 days before the medium was harvested. After dialysis against buffer A (50 mM sodium phosphate; 300 mM NaCl; pH 7.4), supernatants were incubated with Talon resin (Clontech) and the native buffer protocol provided. After washing, the fusion protein was eluted with buffer A containing 150 mM imidazole. The fractions containing SLURP-1 were either dialysed against buffer A or loaded on a BioRad BioPrepSE-100/17gel filtration chromatography column and eluted with buffer A to obtain pure recombinant SLURP-1.

Figure 2:
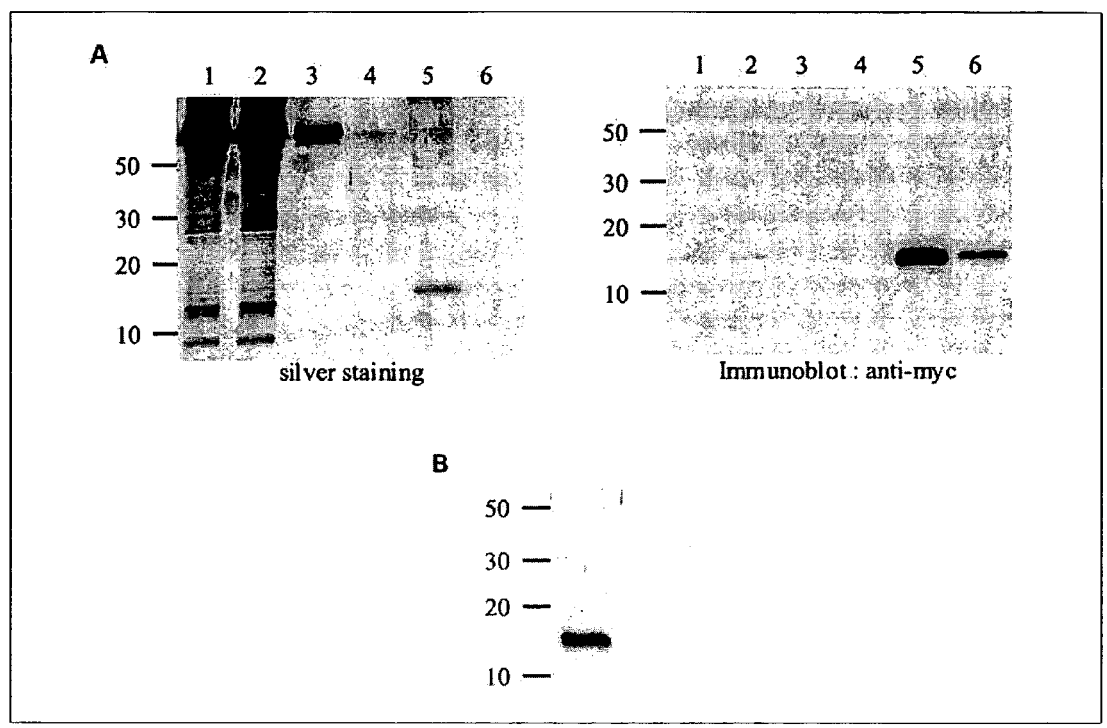
FIGS. 2A and 2B are photographs of immunoblots showing the purification of SLURP-1.

FIG. 2A shows the 293T-SLURP-1 stable cell line generated by calcium phosphate transfection and Zeocin selection. Culture medium was collected after 72 h. His6-tagged SLURP-1 was purified from culture medium with Talon resin. Fractions were loaded on a 15% SDS-PAGE. Proteins were revealed either by silver staining or immunoblotted with anti-myc antibody. Lane 1, input; lane 2, flow-through; lane 3, wash 1; lane 4, wash 2; lane 5, elution 1; lane 6, elution 2. The results in FIG 2A show that most proteins did not bind the resin, and remained in the flowthrough fraction.

FIG. 2B shows silver stained SDS-PAGE (15% acrylamide) of recombinant SLURP-1 following purification with Talon resin and size exclusion chromatography. The results in FIG. 2B show that co-purified proteins were eliminated by gel filtration (BioRad BioPrepSE-100/17) and pure recombinant SLURP-1 was obtained. The estimated final yield was about 100 μg of protein per liter of culture medium.

Example 2

Since protein glycosylation can change biological properties and since SLURP-1 contains a putative N-glycosylation site on N64, partially purified SLURP-1 was produced in mammalian and insect cells was incubated with N-glycosidase F, which hydrolyses N-glycan chains. Specifically, approximately 10 mg of myc-His6-tagged SLURP-1 partially purified either from insect or mammalian cells culture medium was diluted in a solution of 25 mM sodium phosphate (pH 7.0), 25 mM EDTA, and 0.15% SDS and then heated at 100° C. for 5 min. After the solution cooled, 10% Nonidet P-40 and 0.6 U N-glycosidase F (Roche) were added (final detergent concentrations, 0.1% SDS and 0.5% Nonidet P-40) and the mixture was incubated at 37° C. for 20 h. The reaction was stopped by adding SDS-PAGE sample buffer, followed by incubation at 100° C. for 5 min. Samples were then loaded in 15% SDS-PAGE and revealed with silver staining or western blotting with anti-myc antibody, using co-purified proteins as internal positive control for N-glycosidase F activity. The shift in the migration in some of these co-purified proteins indicated the proper functioning of the enzyme. The arrow in FIG. 1C indicates co-purified deglycosylated protein not present before N-glycosidase treatment. The results in FIG. 1C show that N-glycosidase treatment did not modify the migration of SLURP-1, indicating that SLURP-1 is not glycosylated.

Example 3

Figure 3:
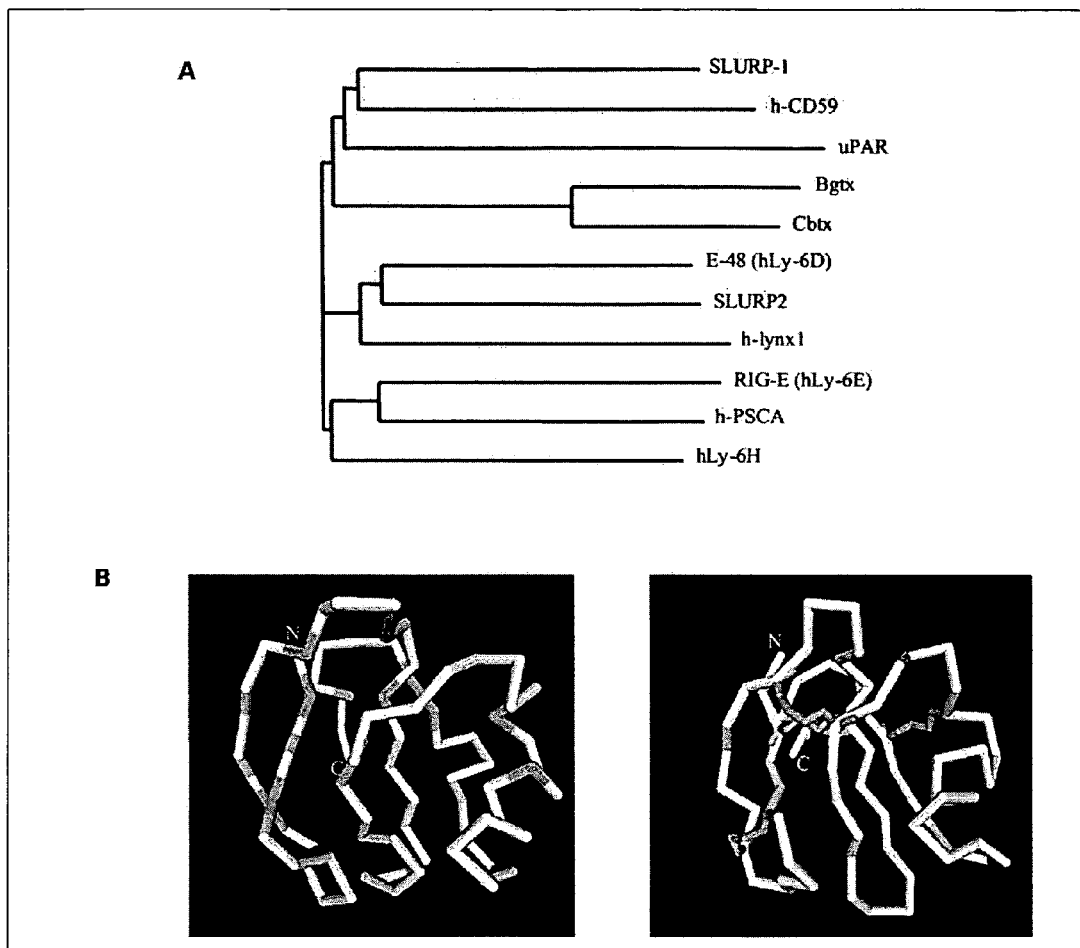
FIG. 3A is a schematic representation and FIG. 3B is the corresponding three-dimensional model showing the structural homology between SLURP-1, members of the Ly-6/uPAR family and various snake venom toxins.
Figure 4:
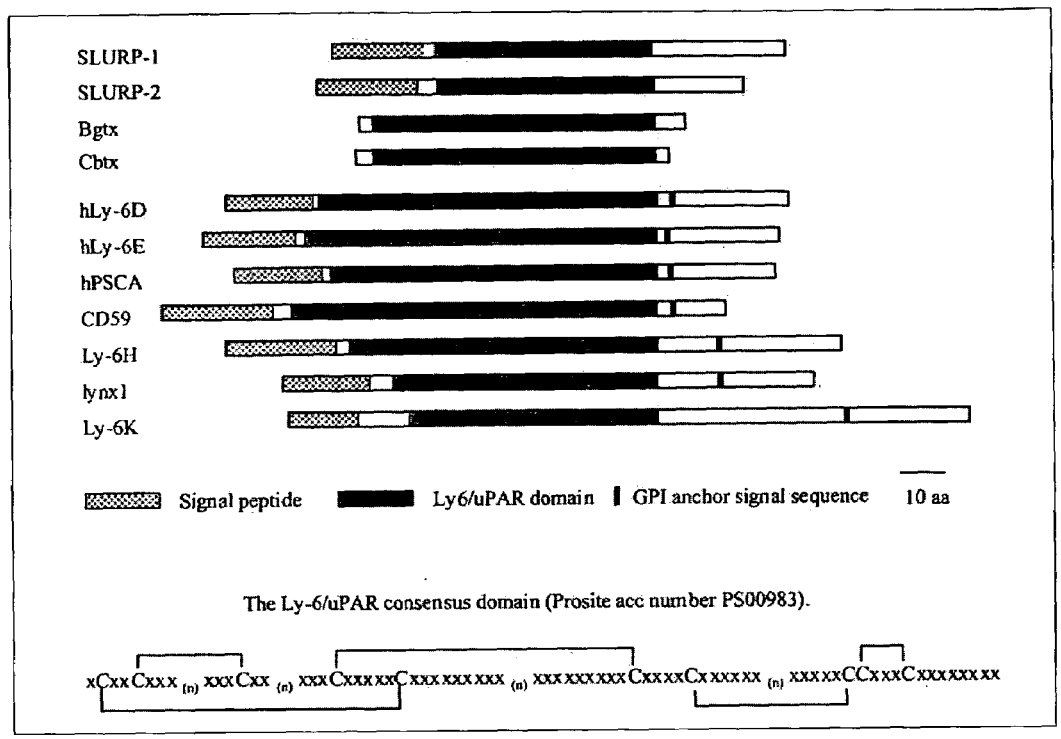
FIG. 4 is a schematic showing the homology comparisons between members of the Ly-6/uPAR family and various snake venom toxins.

Because SLURP-1 is member of the Ly-6/αBgtx families, structural analysis studies were conducted to determine the similarity of SLURP-1 to other proteins. FIG. 3A shows a phylogenetic tree of the Ly-6/αBgtx families indicating the relationship between secreted snake toxins and the GPI-anchored Ly-6/uPAR family. Phylogenetic tree calculation is based on a sequence distance method and utilizes the neighbor joining algorithm (See, Saitou and Nei, Mol. Biol. Evol., 4, 406–425 (1987). FIG. 4 shows the comparison of domain constitution between members of the Ly-6/uPAR family and snake venom toxins. All of the proteins of the family share the same consensus domain. uPAR shares the same structure but also contains three contiguous Ly-6/uPAR domains. The GPI anchor signal sequence indicates cleavage site after addition of GPI moiety. The data in FIG. 3A and in FIG. 4 show that phylogenetic analysis based on the SLURP-1 amino acid sequence reveals a close relationship to the subfamily of single domain snake and frog cytotoxins, i.e. a-bungarotoxin. The data further shows that SLURP-1 is phylogenetically more closely related to snake toxins than it is to the mammalian GPI-anchored receptors.

To further analyze the structure of SLURP-1, a three dimensional model was generated. Specifically, three dimensional model of SLURP-1 was built by the computer program 3D-PSSM (See, Kelley et al., J. Mol. Biol., 299, 499–520 (2000)). 3D-PSSM (three-dimensional position-specific scoring matrix) uses structural alignments of homologous proteins of similar three-dimensional structure in the structural classification of proteins (SCOP) database to obtain a structural equivalence of residues. These equivalences are used to extend multiply aligned sequences obtained by standard sequence searches. The resulting large superfamily-based multiple alignment is converted into a PSSM. Combined with secondary structure matching and solvation potentials, 3D-PSSM can recognize structural and functional relationships between homologous proteins (See, Kelley et al., J. Mol. Biol., 299, 499–520 (2000)). FIG. 3B shows the comparison of the SLURP-1 model (left) and the CD59 extracellular domain experimental NMR structure (right, PDB code: 1ERG). SLURP-1 cysteines are colored in yellow, as disulfide bridges of the CD59 extracellular domain. The data indicates the homologous disposition of CD59 disulfide bridges and SLURP-1 cysteines. Both proteins structurally adopt, or are predicted to adopt, the characteristic 'three-finger' appearance of snake proteins. N- and C-terminal ends of the molecules are labeled. The three-dimensional structure analysis of SLURP-1 in FIG. 3B shows that SLURP-1 resembles the three-dimensional structure of other Ly-6 proteins and three-fingered frog and snake venom toxins, i.e. CD59 and a-bungarotoxin.

Example 4

A study was performed to determine whether SLURP-1 interacts with nicotinic acetylcholine receptors and is functionally homologous to the venom toxins. In the study, acetylcholine-elicited macroscopic current responses in control and SLURP-1-treated *Xenopus* oocytes expressing recombinant human a7 nicotinic acetylcholine receptors were examined.

Specifically, *X. laevis* oocytes were isolated and prepared as described previously (See, Bertrand et al., In: Methods in Neuroscience, Conn, M. (ed.). Academic Press, New York, Vol. 4, pp. 174–193 (1991)). Oocytes were intranuclearly injected with 2 ng of human a7 cDNA and kept in separate wells of a 96-well microtitre plate at 18° C. OR2 control medium consisted of 88 mM NaCl, 2.5 mM KCl, 10 mM HEPES, 1 mM $MgCl_2$, and 2 mM $CaCl_2$, pH 7.4, adjusted with NaOH. Electrophysiology experiments were carried out 2–4 days after cDNA injection. Electrophysiological recordings were performed using a two-electrode voltage-clamp (GeneClamp amplifier; Axon Instruments, Union City, Calif., USA); holding potential was—100 mV. Electrodes were pulled from borosilicate glass and contained 3M KCl. Solution exchanges were performed by an automated system based around a liquid handling robot. Oocytes were continuously superfused with OR2 except during peptide incubation. Oocytes were maintained at 18° C. during experiments. Dose-response curves were fit by the equation $y=I_{max}*\{1/(1+(EC_{50}/[Ach])^n)\}$, where $I_{max}$ is the maximal normalized current amplitude, EC50 the half effective agonist concentration, n the Hill coefficient and [Ach] the Acetylcholine concentration.

Figure 5:
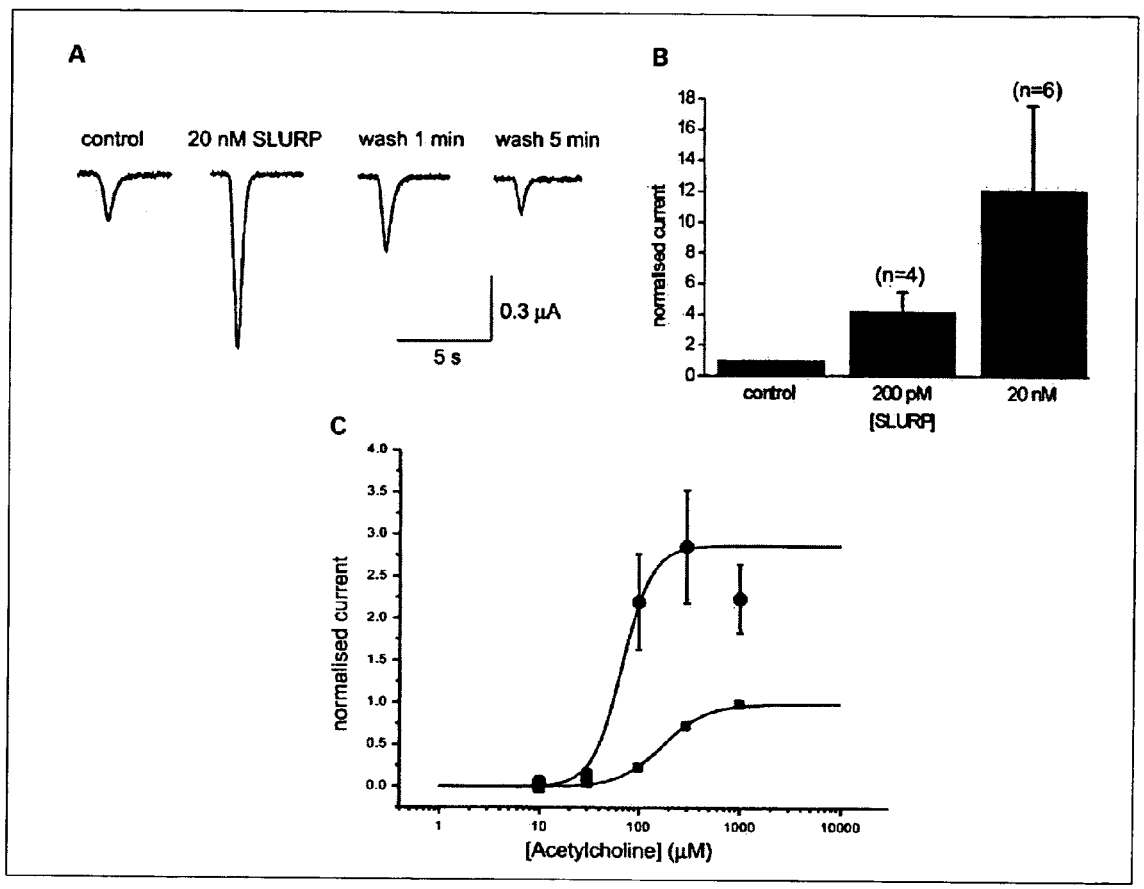
FIG. 5A is an electrophysiological recording and FIGS. 5B and 5C are corresponding bar and line graphs showing that SLURP-1 modulates the activity of acetylcholine receptors.

Acetylcholine-evoked responses were measured before and after exposure (2.5–5 min) to highly purified SLURP-1. SLURP-1 enhanced the amplitude of the Acetylcholine-evoked macroscopic currents in a concentration-dependent manner. FIG. 5A shows current responses before and after 5 min exposure to 20 nM SLURP-1. Currents were activated by a 2s application of 100 mM Acetylcholine. The results in FIG. 5A show that at a concentration of 200 pM, SLURP-1 increased the amplitude of the Acetylcholine-evoked macroscopic currents by 421±130% (n=6), and 20 nM SLURP-1 enhanced the amplitude by 1214±550% (n=4), compared with control. As shown in FIG. 5B, the dose-response curve indicates that SLURP-1 potentiates a7 nicotinic acetylcholine receptor homopentamers, since the $EC_{50}$ was 175 μM acetylcholine for the controls and dropped to 68 μM Acetylcholine after SLURP-1 treatment. FIG. 5C shows that 200 pM SLURP-1 shifted the Acetylcholine dose response curve (closed squares) to the left and increased Emax (solid circles). EC50 was 178 μM for control and 68 μM after 2.5 min exposure to SLURP-1 (200 pM). n=6 for each data point. The effects of SLURP-1 on the Acetylcholine dose-response curve indicate that 200 pM causes an increase in both current amplitude and sensitivity to Acetylcholine as well as an increase in the Hill coefficient. Application of SLURP-1 did not evoke currents in the absence of Acetylcholine. Thus, SLURP-1 functions not as a ligand or neurotransmitter, but modulates receptor function in the presence of its natural ligand in a manner consistent with an allosteric mode of action.

Example 5

To further characterize the electrophysiology of SLURP-1 activity on acetylcholine receptors and identify the site of interaction, chimeric-subunits are constructed from α7 and subunits that are not potentiated by SLURP-1 and express them in *X. laevis* oocytes. The specific amino acid residues implicated in the action of SLURP-1 are identified using α7 subunits containing single point mutations. Electrophysiological studies are extended to keratinocytes in culture and other cell types expressing the acetylcholine receptor target of SLURP-1. The impact of SLURP-1 on keratinocyte differentiation is studied in organotypic skin cultures.

The interaction of SLURP-1 with acetylcholine receptors is characterized at the molecular level. The effects of the mutated SLURP-1 proteins is compared to those of native SLURP-1 on homomeric and heteromeric acetylcholine receptors. Identification of residues essential for interaction of SLURP-1 with its target(s) facilitates the design of molecules either mimicking or antagonizing the effect of SLURP-1 since interaction of three finger toxins with their target often involves only a few amino acids, either clustered or spread along the primary structure of the proteins (See, Kini, Clin Exp Pharmacol Physiol 29(9): 815–22 (2002)).

To determine the in situ localization of SLURP-1 and its transcripts, in situ hybridization studies are carried out on human biopsies using anti-SLURP-1 antibodies. Monoclonal and polyclonal anti-SLURP-1 antibodies can be generated to specific domains (i.e. internal domain) of SLURP-1 for these and additional studies. These studies will complement immunohistochemical studies localizing SLURP-1 in various epithelia (See, Mastrangeli and Donini, Eur J Dermatol 13(6): 560–70 (2003)). These studies will identify altered expression of SLURP-1 in certain pathologies, e.g., dermatological disorders.

To determine the effective of SLURP-1 on gene expression in vivo, human biopsies and SLURP-1 transgenic mice are subjected to microarray analysis. The expression of SLURP-1 in these transgenic mice is under the control of keratin 14 promoter (basal layer expression). These studies allow for the identification of the exact physiological effects of SLURP-1 in vivo.

Example 6

To determine the activity of other secreted Ly-6/uPAR family members (Lynx-1 Isoform A, Lynx-1 Isoform B and RGTR-430), Ly-6/uPAR family member recombinant proteins expressing c-myc and $His_6$ tags are generated as described (See, Example 1, supra, and Chimineti et al., Hum Mol Genet 12(22): 3017–24 (2003)). These Ly-6/uPAR family member recombinant proteins are purified to apparent homogeneity in two steps by immobilized metal affinity chromatography and gel filtration as described (See, Example 1, supra; Chimineti et al., Hum Mol Genet 12(22): 3017–24 (2003); Ibanez et al., Neuron 33(6): 893–903 (2002)). Further, monoclonal and polyclonal antibodies are generated to specific secreted Ly-6/uPAR family member proteins. These antibodies can be generated to specific domains. Alternatively, since homology among secreted Ly-6/uPAR family member proteins is low, rabbits can be immunized with complete proteins or GST-fusion proteins.

Various tissues have been analyzed to determine the expression of genes encoding the secreted Ly-6/uPAR family members using RT-PCR. Studies show that transcripts for SLURP-1, RGTR-430 and Lynx-1 Isoform B are highly expressed in the epidermis and in normal human keratinocytes in culture; while the expression of Lynx-1 transcript 3, coding for the GPI-anchored Isoform C, is much more ubiquitously expressed. Further, the effects of secreted Ly-6/uPAR family member proteins can be assessed on ligand-gated ion channels expressed in *X. laevis* oocytes to identify their action on acetylcholine receptor activity as described (See, Example 4, supra; Chimineti et al., Hum Mol Genet 12(22): 3017–24 (2003).

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating schizophrenia in a subject suffering therefrom, the method comprising administering to the subject an effective amount of a SLURP-1 polypeptide comprising the amino acid sequence of SEQ ID NO: 2, thereby treating schizophrenia in the subject.

2. A method for treating schizophrenia in a subject suffering therefrom, the method comprising administering to the subject an effective amount of a SLURP-1 polypeptide comprising amino acids 23–103 of the amino acid sequence of SEQ ID NO: 2, thereby treating schizophrenia in the subject.

3. The method of claim 2, comprising administering to the subject an effective amount of a SLURP-1 polypeptide consisting of amino acids 23–103 of SEQ ID NO: 2.

4. A method for treating schizophrenia in a subject suffering therefrom, the method comprising administering to the subject an effective amount of a SLURP-1 polypeptide at least 95% identical to the amino acid sequence of SEQ ID NO:2 and wherein the polypeptide enhances the amplitude of acetylcholine-evoked macroscopic currents, thereby treating schizophrenia in the subject.

5. The method of claim 4, wherein the SLURP-1 polypeptide is at least 99% identical to the amino acid sequence of SEQ ID NO:2.

6. The method of claim 1, 2, 3, 4 or 5 wherein the effective amount of the SLURP-1 polypeptide is from about 1.0 pM to about 10 µM.

7. The method of claim 1, 2, 3, 4 or 5 wherein the effective amount of the SLURP-1 polypeptide is administered to the subject by a method selected from the group consisting of orally, intravenously, intraperitoneally, intranasally, and intramuscularly.

* * * * *

SEQUENCE LISTING

```
<160> NUMBER OF SEQ ID NOS: 6

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence:  Consensus
      Domain Sequence
<220> FEATURE:
<221> NAME/KEY: VARIANT
<222> LOCATION: (3)..(6)
<223> OTHER INFORMATION: Wherein Xaa is any amino acid.

<400> SEQUENCE: 1

Cys Cys Xaa Xaa Xaa Xaa Cys Asn
  1               5

<210> SEQ ID NO 2
<211> LENGTH: 103
<212> TYPE: PRT
<213> ORGANISM: Homo sapiens

<400> SEQUENCE: 2

Met Ala Ser Arg Trp Ala Val Gln Leu Leu Leu Val Ala Ala Trp Ser
  1               5                  10                  15
```

```
Met Gly Cys Gly Glu Ala Leu Lys Cys Tyr Thr Cys Lys Glu Pro Met
            20                  25                  30

Thr Ser Ala Ser Cys Arg Thr Ile Thr Arg Cys Lys Pro Glu Asp Thr
        35                  40                  45

Ala Cys Met Thr Thr Leu Val Thr Val Glu Ala Glu Tyr Pro Phe Asn
    50                  55                  60

Gln Ser Pro Val Val Thr Arg Ser Cys Ser Ser Ser Cys Val Ala Thr
65                  70                  75                  80

Asp Pro Asp Ser Ile Gly Ala Ala His Leu Ile Phe Cys Cys Phe Arg
                85                  90                  95

Asp Leu Cys Asn Ser Glu Leu
            100

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Primer
      Sequence

<400> SEQUENCE: 3
aagcttggag caatggcctc tcgctgg                                        27

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Primer
      Sequence

<400> SEQUENCE: 4
tctagagagt tccgagttgc agaggtc                                        27

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Primer
      Sequence

<400> SEQUENCE: 5
gagatatcgg agcaatggcc                                                20

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Primer
      Sequence

<400> SEQUENCE: 6
agagatcttc acagatcctc ttctgagatg                                     30
```